United States Patent
Durack

(10) Patent No.: US 7,590,221 B2
(45) Date of Patent: Sep. 15, 2009

(54) METHOD AND APPARATUS FOR ANGLE OF INCLINATION ACQUISITION AND DISPLAY ON RADIOGRAPHIC IMAGE

(75) Inventor: Jeremy C. Durack, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/965,495

(22) Filed: Dec. 27, 2007

(65) Prior Publication Data

US 2008/0175353 A1  Jul. 24, 2008

Related U.S. Application Data

(63) Continuation of application No. PCT/US2006/025720, filed on Jun. 30, 2006.

(60) Provisional application No. 60/696,040, filed on Jul. 1, 2005.

(51) Int. Cl.
*H05G 1/28* (2006.01)

(52) U.S. Cl. ........................ 378/165; 378/162; 378/204

(58) Field of Classification Search ................ 378/98.8, 378/162, 165, 167, 189, 204, 205; 250/370.09
See application file for complete search history.

(56) References Cited

U.S. PATENT DOCUMENTS

| | | | |
|---|---|---|---|
| 6,092,928 A * | 7/2000 | Mattson et al. | 378/205 |
| 6,556,698 B1 | 4/2003 | Diano et al. | |
| 6,890,099 B2 * | 5/2005 | Tanaka et al. | 378/205 |
| 7,046,764 B1 * | 5/2006 | Kump | 378/117 |
| 7,203,278 B2 * | 4/2007 | Wendt et al. | 378/98.8 |
| 7,447,565 B2 * | 11/2008 | Cerwin | 700/279 |
| 2002/0136356 A1 | 9/2002 | Vallin et al. | |
| 2002/0188416 A1 | 12/2002 | Zhou et al. | |
| 2005/0058244 A1 | 3/2005 | Tanaka et al. | |

* cited by examiner

*Primary Examiner*—Allen C. Ho
(74) *Attorney, Agent, or Firm*—John P. O'Banion

(57) ABSTRACT

A device is shown for measuring the angle of inclination of a radiographic imaging cassette. The device has a digital inclinometer, such as a MEMS accelerometer, configured to measure the angle of inclination of the cassette with respect to gravity. The device may be portable, including a display coupled to the inclinometer for indicating the angle of inclination of the cassette. The display may be a digital readout, or an analog meter having radio-opaque gradations such that the angle of inclination is recorded on an image processed from the imaging cassette. Alternatively, the digital inclinometer may be integrated into the imaging cassette, and be configured such that readings from the digital inclinometer may be uploaded to a digitizer via an RF transmitter or other transmission means.

30 Claims, 7 Drawing Sheets

METHOD AND APPARATUS FOR ANGLE OF INCLINATION ACQUISITION AND DISPLAY ON RADIOGRAPHIC IMAGE

CROSS-REFERENCE TO RELATED APPLICATIONS

This application claims priority from, and is a 35 U.S.C. § 111(a) continuation of, co-pending PCT international application serial number PCT/US2006/025720, filed on Jun. 30, 2006, incorporated herein by reference in its entirety, which claims priority from U.S. provisional application No. 60/696,040, filed on Jul. 1, 2005, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

This invention pertains generally to apparatus and method for recording angle of inclination of a radiographic cassette, and more particularly to recording angle of inclination of a radiographic cassette with a digital inclinometer.

2. Description of Related Art

Knowledge of the angle of inclination of an imaged object can be extremely important for interpretation of object states. Accurate interpretation of imaging studies by a diagnostic radiologist, particularly x-ray studies of the chest and abdomen, requires knowledge of the patient state at the time of image exposure. For example, the thorax, abdomen, or other body part of a patient is typically oriented from 0° to 90° relative to the ground at the time of an imaging study, often a conventional x-ray. The vector force of gravity exerted upon imaged structures that are mobile (for example soft tissue structures, gaseous particles, and liquids) will vary according to the angle of inclination of these structures with respect to the gravitational force.

Conventional x-ray studies are currently presented for interpretation in a 2-dimensional format, either on film or a computer monitor, effectively flattening the anterior-posterior diameter of the imaged object. A device that accurately reports the angle of the photoreceptor at the time of imaging (in the case of diagnostic radiology, the film or imaging cassette 10 as shown in FIG. 1) enables more informed analysis of a 2-dimensional image, because the relative effect of the gravitational force can be integrated into its interpretation. Without knowledge of patient positioning, interpretation of diagnostic imaging studies is limited and can in fact be misleading. Clinical management often relies heavily on radiographic interpretations in patients ranging from the critically ill hospitalized patient to the ambulatory outpatient.

Portable x-rays are taken on the wards by radiology technologists with a portable x-ray device 12, shown in FIG. 2. A storage tray within this device contains multiple digital or film-based cassettes 10 which are transported back to a centralized digitizer 14 (FIG. 3) once exposed. Imaging cassettes typically range from approximately 10.5×10.5 inches to 13×15 inches or larger. Most cassettes are constructed from thick plastic-like material.

Standard digital imaging cassettes contain either a photostimulable phosphor plate or scintillator that ultimately converts x-ray photons into light. In the processing of digital imaging cassettes, the amount of light (proportional to incident x-ray exposure) is recorded and a digital file containing the two dimensional image matrix is generated. Film-based cassettes may be digitized subsequent to standard film processing.

The digitizer typically houses a computer terminal for entry of patient information (name, medical record number, ward, study indication, etc.) and image information (x-ray type, exposure energy, etc.). This can be done either manually by keyboard entry, or frequently automatically by barcode-type scanning of the imaging study requisition printout. Digitizers are designed to be "drop-and-go" devices that allow the technologist to insert the cassette, wait a moment for the imaging plate to be processed and erased, then either insert the next cassette or move on to the next task.

Digital files are created by the digitizer and transferred via network communications to the hospital PACS (Picture Archiving and Communication System) for viewing on a monitor by the radiologist. Standards for information exchange related to an imaging study have been established by the National Electrical Manufacturers Association (NEMA) in collaboration with radiologists, termed Digital Imaging and Communications in Medicine (DICOM). These DICOM standards allow the PACS system to recognize the various components of the imaging file (name, medical record number, study accession number, exposure parameters, etc.) in order to display these data for initial interpretation, subsequent archival, and later retrieval (of utmost importance for transferring studies to other institutions and for comparison with prior studies at a later date).

Referring to FIG. 4, some brands of digital cassettes 10 contain a built-in chip 16 that stores a unique identification number for each cassette. The cassette identifier number is typically uploaded to the digitizer by radiofrequency or other mode of wired or wireless data transmission for cassettes when inserted into the digitizer.

Currently, imaging cassette angle is measured, but only crudely and inconsistently. A commonly available imaging angle detector consists of a small plastic reservoir (shallow cup) containing three small metallic balls. Many radiology technicians performing x-ray examinations, film-based or digital, carry such a marker. If the balls are grouped together in the middle of the circle, it is presumed that the patient is flat (supine). If layered at the bottom of the reservoir, then it is assumed that the imaging cassette (and thus the patient) is in an elevated position with a wide range between 1° and 90°. Patient position may also be crudely indicated by the radiology technologist obtaining the x-ray. Radioopaque markers may be placed over the imaging cassette crudely indicating patient position using an arrow or labels, such as "supine," "upright," or "semi-erect." For the diagnostic radiologist, these inconsistent and non-standardized techniques render the current method of cassette angle reporting relatively ineffectual.

Accordingly, an object of the present invention is to provide imaging angle detection and reporting to complement current radiographic imaging, and thus improve imaging technique and interpretative/diagnostic accuracy.

A further object is an imaging cassette with an indicator that signals prior exposure of the cassette array to x-rays.

At least some of these objectives will be met in the invention described hereafter.

BRIEF SUMMARY OF THE INVENTION

Methods and apparatus are described for measuring and recording the angle of an imaging cassette (film-based, computed radiography, or digital radiography) at the time of exposure with respect to the ground (perpendicular to the direction of the force of gravity). The imaging angle detector reports the angle of imaging cassette as a proxy for the orientation of the imaged object, typically a human or veterinary patient in the field of diagnostic radiology.

An aspect of the invention is an apparatus for measuring the angle of inclination of a radiographic imaging cassette. The apparatus comprises a digital inclinometer, such as a microelectromechanical system (MEMS) accelerometer, configured to measure the angle of inclination of the cassette with respect to gravity, and a display coupled to the inclinometer for indicating the angle of inclination of the cassette. The apparatus also has a power source, such as a battery, for delivering power to the digital inclinometer.

The display may comprise a digital readout, or an analog meter having radio-opaque gradations such that the angle of inclination is recorded on an image processed from the imaging cassette. The analog meter may be configured to indicate angular inclination based on an analog voltage output from the digital inclinometer, e.g., by scaling the angle of inclination linearly with the analog output voltage.

The apparatus may be configured to interface directly with a digital imaging cassette or a film-based imaging cassette, and may have means for detachably mounting the digital inclinometer to the imaging cassette.

Another aspect of the invention is a radiographic imaging cassette having an imaging plate responsive to radiographic photons and a casing supporting the imaging plate. A digital inclinometer configured to measure the angle of inclination of the cassette with respect to gravity is coupled to the casing. The imaging cassette further includes a memory module or radiofrequency tag coupled to the digital inclinometer, a power source for delivering power to the digital inclinometer and memory module, and an output for communicating angle of inclination data to a digitizer.

The output may be a physical port, such as a USB (universal serial bus) connection, or a wireless device such as a RF (radio frequency) transmitter. The output may also be configured to transmit additional data, such as imaging cassette identifiers or patient specific data.

In one embodiment, the angle of inclination data is configured to be mapped as a DICOM tag.

In another embodiment, a sensor may be coupled to the digital inclinometer, wherein the sensor detects exposure to radiographic waves. Preferably the sensor is configured to initiate a reading from the digital inclinometer. The sensor may also be coupled to an indicator for signaling exposure of the cassette to radiographic waves. Alternatively, a manual switch may be used to initiate a reading from the digital inclinometer. The switch may also be coupled to an indicator for signaling exposure of the cassette to radiographic waves.

Another aspect of the invention is a method for reporting angle of inclination of a radiographic imaging cassette. The method includes the steps of measuring the angle of inclination of the imaging cassette with respect to gravity via an accelerometer, wherein the accelerometer generates an electric signal corresponding to the angle of inclination with respect to gravity, and displaying the angle of inclination of the imaging cassette.

In some embodiments, the accelerometer generates a digital signal corresponding to the angle of inclination of the cassette, such that the angle of inclination is displayed on a digital readout. Alternatively, the accelerometer generates an analog signal corresponding to the angle of inclination of the cassette, such that the angle of inclination is displayed on an analog display. In such case, the analog display comprises radio-opaque gradations such that the angle of inclination is recorded on an image processed from the imaging cassette.

A further aspect is a method for reporting angle of inclination of a radiographic imaging cassette, comprising: generating the angle of inclination data of the imaging cassette with respect to gravity via an accelerometer, wherein the accelerometer generates a digital signal corresponding to the angle of inclination with respect to gravity, and uploading the angle of inclination data to a digitizer for processing and display. The angle of inclination data may be stored in a memory module prior to uploading the data to a digitizer.

In one embodiment, the generation of the angle of inclination data is initiated prior to or during exposure of the cassette to a radiographic image, either by detecting the exposure of the cassette to a radiographic image, or manually initiating a reading from the digital inclinometer via a switch. The method may further include visually indicating the detection of exposure of the cassette to the radiographic image.

In another embodiment, a digital file comprising a radiographic image corresponding to the angle of inclination data and the angle of inclination data DICOM tag may be generated. The digital file may be further transmitted to a PACS system for viewing the angle of inclination data simultaneously with the radiographic image.

In yet another aspect, a radiographic imaging cassette comprises an imaging plate responsive to radiographic energy, a casing supporting the imaging plate, and a triggering means coupled to the casing. The imaging cassette further includes an indicator coupled to the triggering means and configured to signal an exposure of the imaging cassette to the radiographic x-rays. The triggering means may comprise a sensor for detecting exposure of the imaging cassette to the radiographic x-rays such that the indicator illuminates upon triggering of the sensor. Alternatively, the triggering means may comprise a manual switch configured to be engaged prior to exposure of the imaging cassette to the radiographic x-rays such that the indicator illuminates upon engaging the manual switch.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

DETAILED DESCRIPTION OF THE INVENTION

Referring more specifically to the drawings, for illustrative purposes the present invention is embodied in the apparatus generally shown in FIG. 5 through FIG. 11. It will be appreciated that the apparatus may vary as to configuration and as to details of the parts, and that the method may vary as to the specific steps and sequence, without departing from the basic concepts as disclosed herein.

Figure 1:
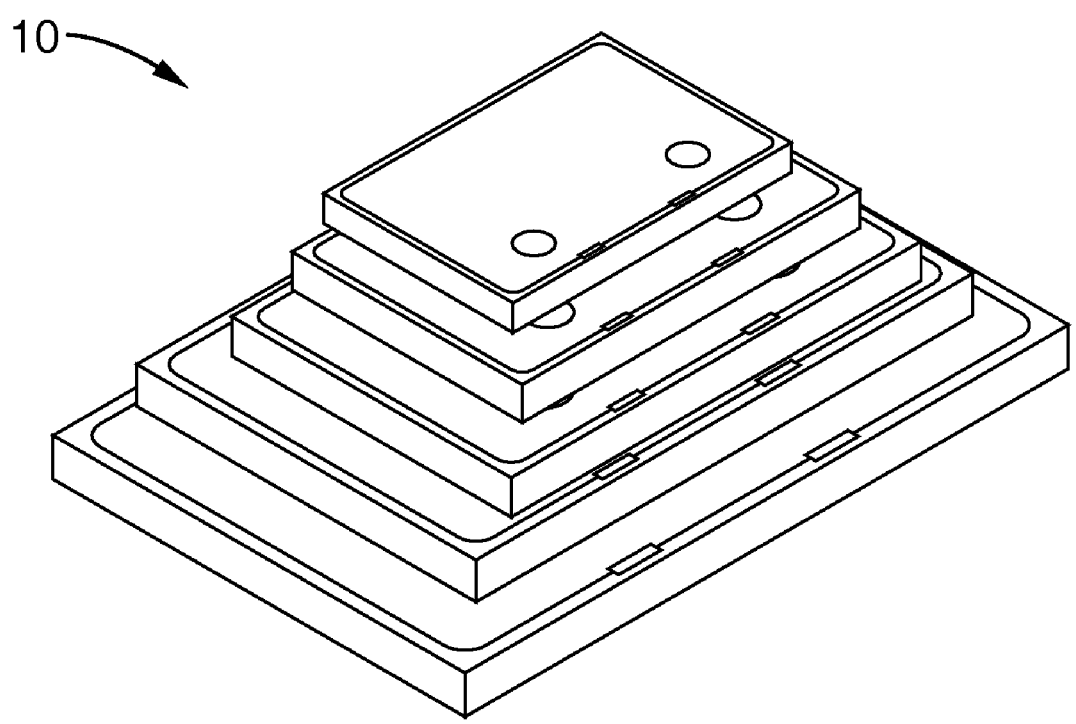
FIG. 1 is an image of a set of radiographic imaging cassettes.
Figure 2:
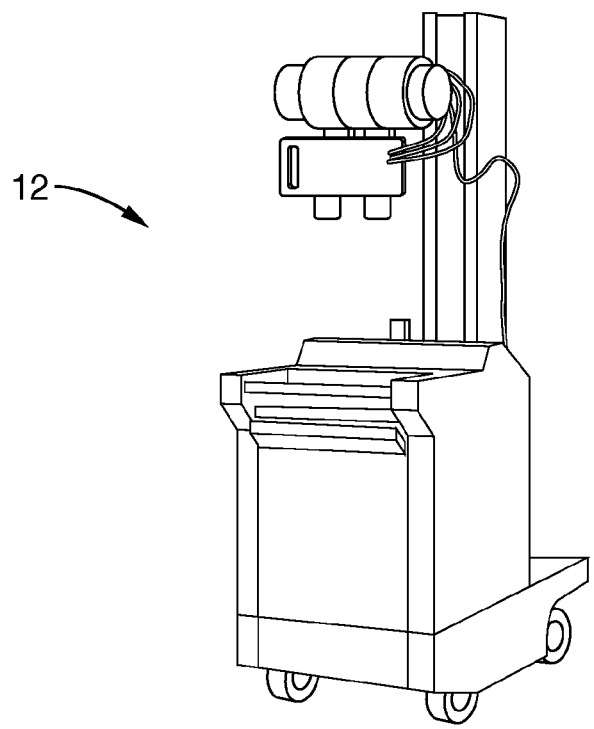
FIG. 2 is an image of a portable x-ray machine
Figure 3:
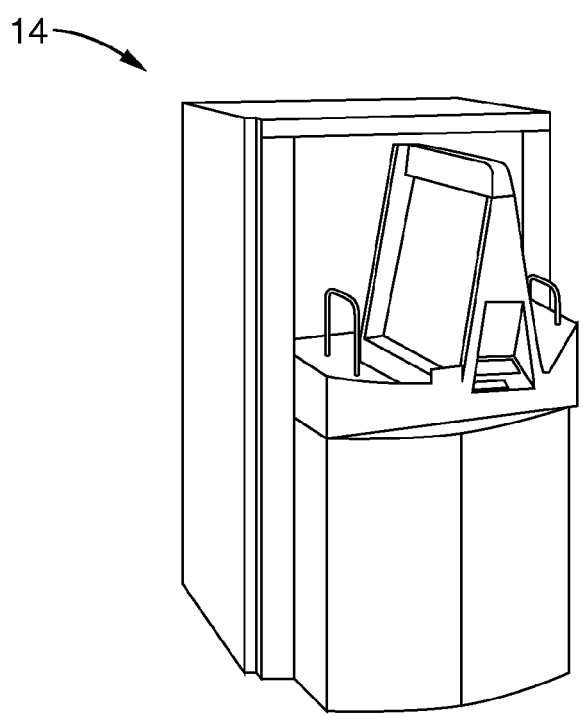
FIG. 3 is an image of a digitizer.
Figure 4:
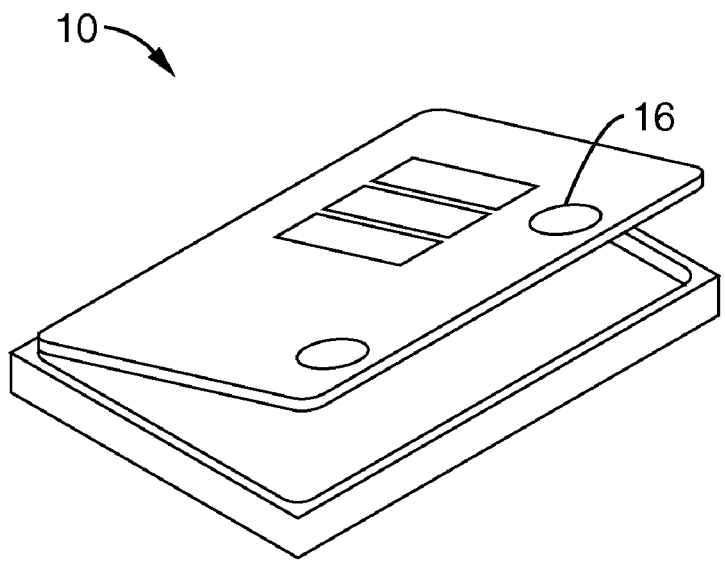
FIG. 4 is an image of a set of radiographic imaging cassettes having an RF ship for transferring data.
Figure 5:
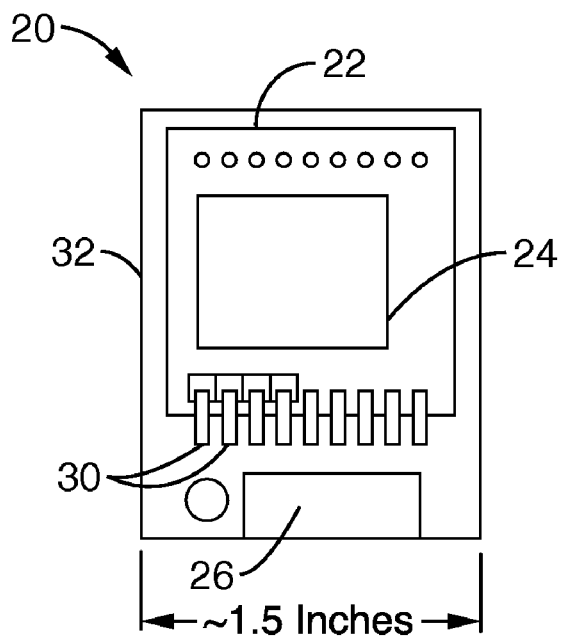
FIG. 5 illustrates a portable, stand-alone inclination display device.
Figure 6:
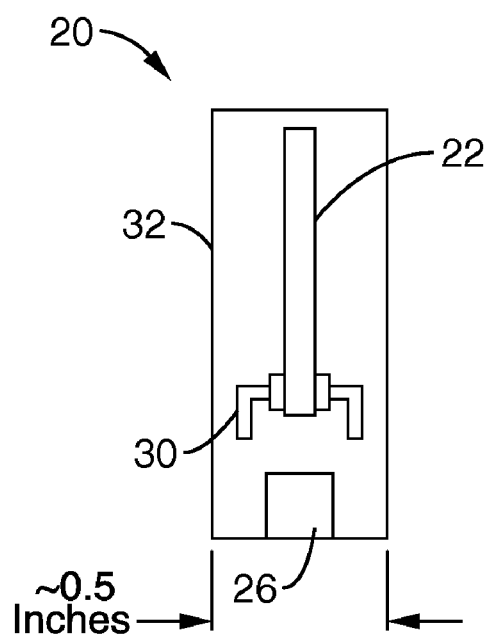
FIG. 6 is a side view of the device shown in FIG. 5.
Figure 7:
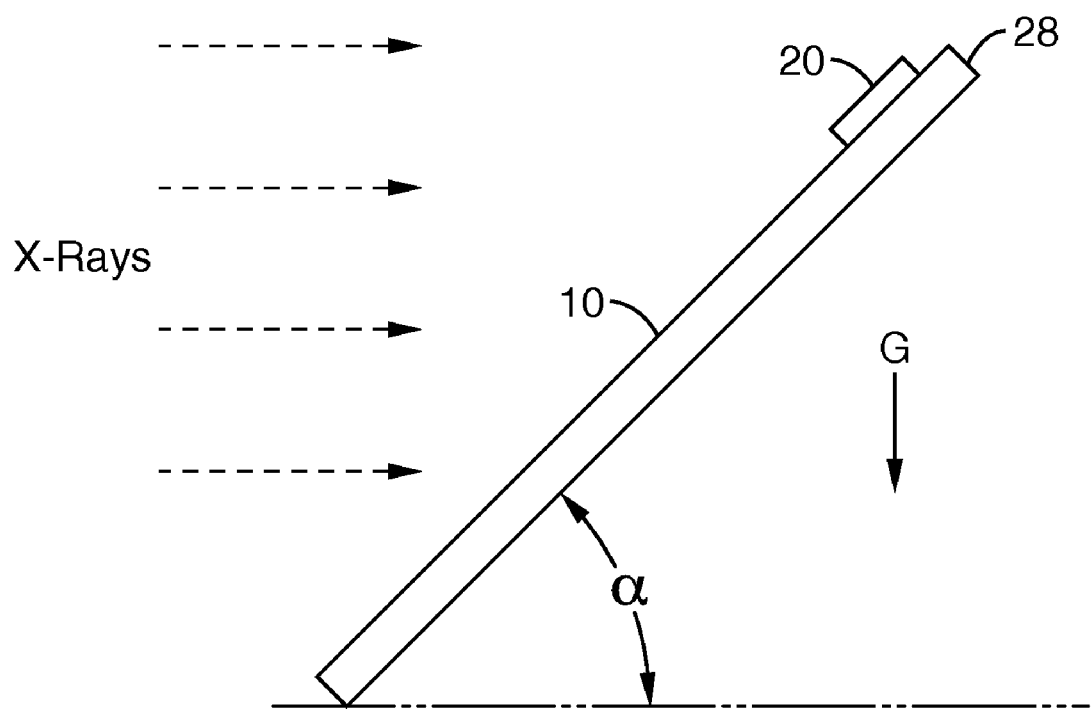
FIG. 7 shows the imaging cassette inclination display device of FIGS. 5 and 6 with a radiographic imaging cassette, in accordance with the present invention.

FIGS. 5, 6, and 7 illustrate a portable, stand-alone inclination display device 20 for use with a radiographic imaging cassette 10 (film or digital) in accordance with the present invention. The portable inclination display device 20 has a digital inclinometer chip 22, and is configured to be repeatedly used during imaging studies. The device 20 may have a clip or other temporary mounting means (e.g., tape) that allows the device to be removably placed on an edge 28 or on a corner of the imaging cassette 10 prior to imaging. The device 10 may have a sturdy casing 32 for housing the inclinometer 22 and a removable battery 26.

The digital inclinometer 22 may be any of a number of currently available chips sold by OEM (original equipment manufacturer) companies (e.g. the SQ-Si-360DA inclinometer by SignalQuest Inc., Lebanon, N.H.). These devices are typically solid-state MEMS (micro-electromechanical system) based accelerometers built into silicon chips, and often accurate to 1° when measuring planar tilt (angle $\alpha$) with respect to gravity. The angle can be measured in either one or two planes. The inclinometer chip 22 comprises a plurality of leads 30 that allow digital input, power from the battery 26, and digital and analog output. The digital output may be coupled to a display means 24, such as an LCD (liquid crystal display) or an LED (light-emitting diode) display, for indicating the cassette angle $\alpha$ at a given time.

The device 20 may be activated at the time of imaging (as is currently done using the existing bead device). The resulting digital report of cassette angle $\alpha$ may then be recorded by the technologist in addition to other imaging parameters.

Once imaging is completed, the device 20 may be removed from the cassette 10 and retained by the physician or technologist for use on a subsequent radiographic image of the same or different patient.

Figure 8:
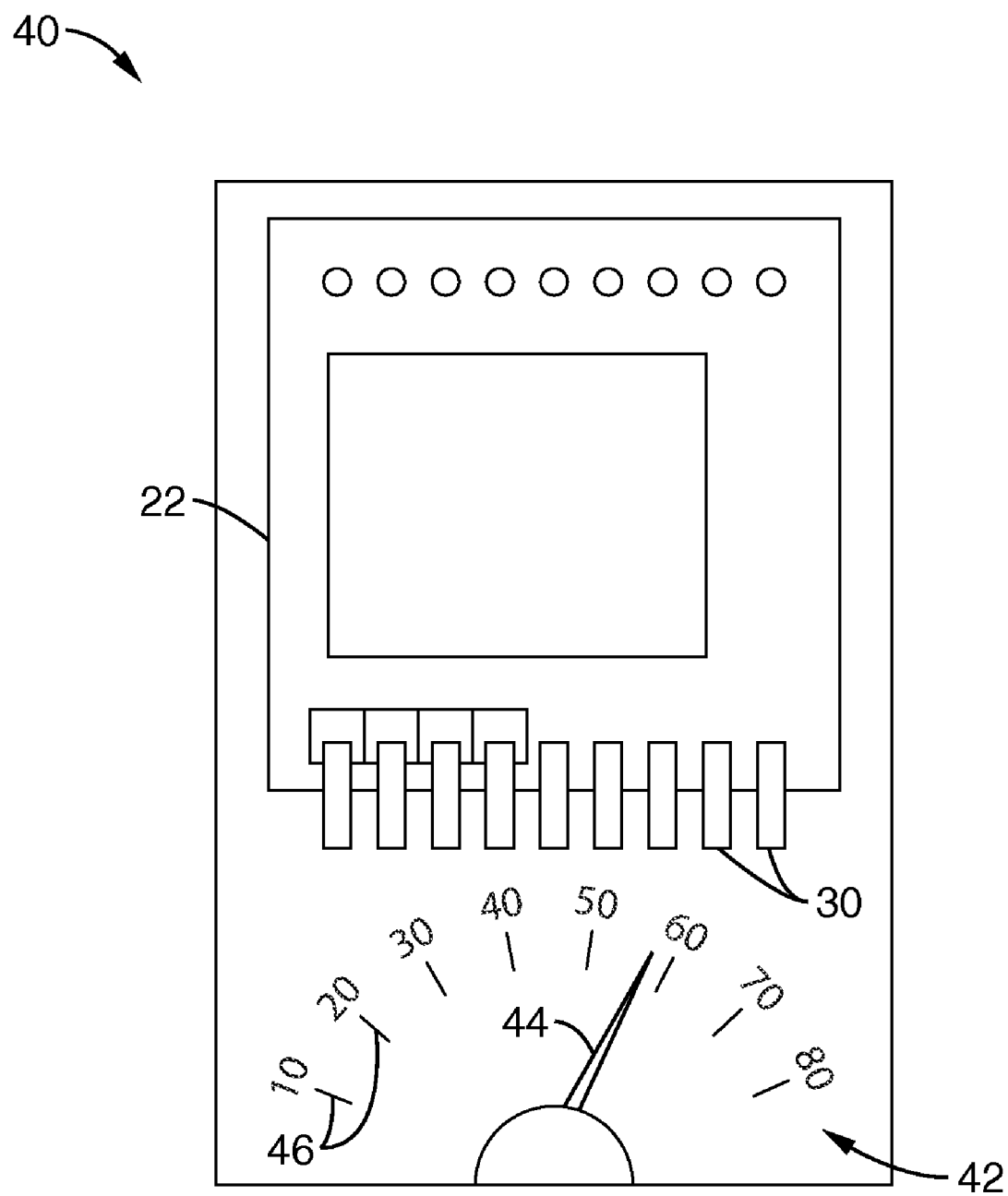
FIG. 8 shows an imaging cassette inclination display device having a digital inclinometer chip and analog display in accordance with the present invention.

FIG. 8 shows an imaging cassette inclination display device 40 having a digital inclinometer chip 22 and an analog display 42. In this configuration, the analog display 42 is coupled to the analog output of leads 30. Device 40 is preferably a low power device with an analog voltmeter adapted to report output voltage as an angle, with the voltage scaling linearly with angle of inclination. The analog meter 42 is preferably fabricated with radio-opaque gradations 46 and radio-opaque needle 44, such that when the device is placed in the corner of an imaging cassette 10, the angle of inclination is permanently recorded on the resulting image. The analog display 40 also has the advantage of automatically recording the inclination angle at the time most important to the radiologist, i.e., the instant the image is taken. Device 40 may also be more reliable than the digital display version of FIG. 5, as the angle reporting requires an additional step on the part of the technologist and may not become permanently associated with the resultant image.

Figure 9:
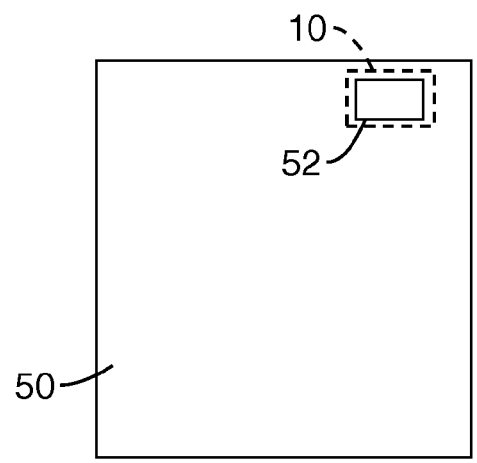
FIG. 9 illustrates a digital imaging cassette having a compact, low-power incline reporting device integrated directly into the imaging cassette in accordance with the present invention.
Figure 10:
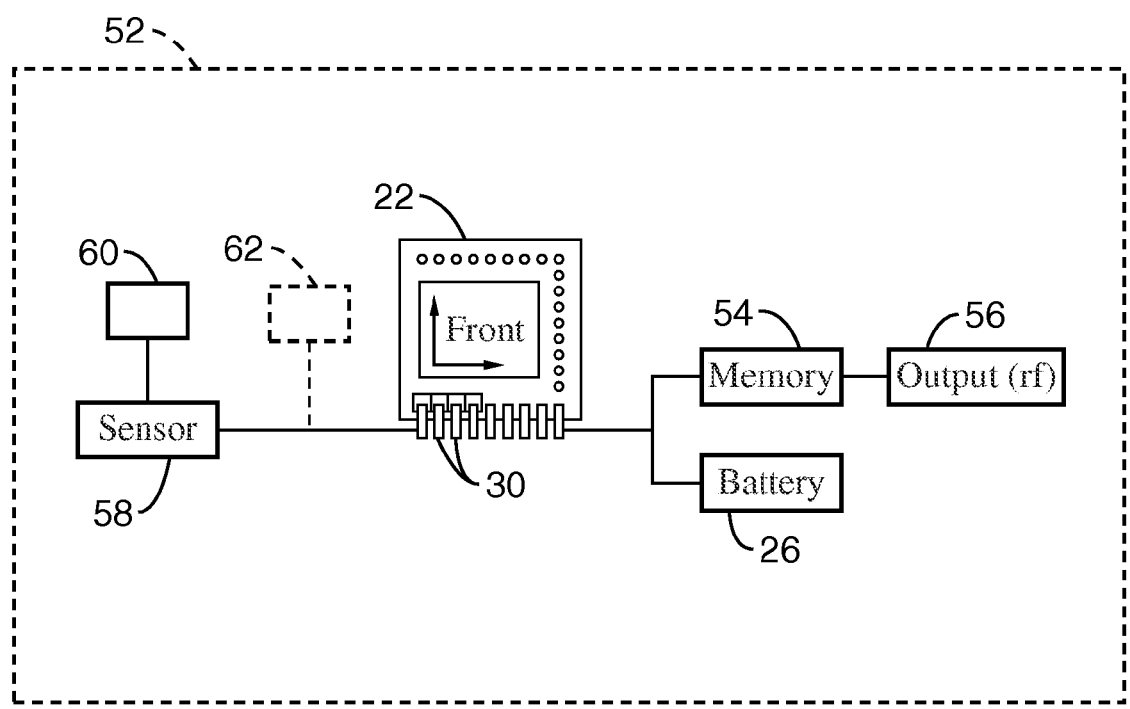
FIG. 10 is an expanded view of the incline reporting device of FIG. 9.

FIGS. 9 and 10 illustrate a digital imaging cassette 50 having a compact, low-power incline reporting device 52 integrated directly into a filmless imaging cassette 50. The incline reporting device 52 is incorporated into the cassette housing to record the angle of inclination at the time of exposure, and subsequently report that data point to the digital processor.

Referring more specifically to FIG. 10, the incline reporting device 52 comprises a digital inclinometer 22 and memory module 54 configured to record, store, and upload information about cassette angle at the time of imaging to the digitizer at the time of cassette processing. Incline reporting device 52 may be configured to include digital signal packet storage, which may be achieved through incorporation of erasable programmable read-only memory (EPROM), flash, or a similar data storage component.

The incline reporting device 52 also includes an output module 56 for passing the angle of inclination, and other information such as time, patient data, etc., from the cassette 50 to the digitizer at the time of processing. The output module 56 may have a wireless transmitter (e.g. an RF or infrared (IR) transmitter), or may comprise a port for connecting a cable to the digitizer (e.g. USB or serial connector). Communication with the digitizer could occur in a number of ways. Some Agfa cassettes currently utilize a radiofrequency signal (RF) to transmit data from the cassettes. Thus, the IR transmitter could also transmit angle data via an RF signal to minimize or obviate any need for modifying the digitizer to be compatible to the cassette 50. Alternatively, the digital cassette 50 could slot into a pin-based docking station within the digitizer for direct transfer of data. Other modes of communication may be possible as well.

Once uploaded, cassette angle information can be mapped to a DICOM tag for incorporation into the digital record for each image and displayed on the PACS workstation at the time of interpretation (existing DICOM tag (0018, 1141) ="Angular Position").

Preferably, activation of the chip 22 is done at the moment that the patient is positioned or x-rays are emitted. To facilitate this timing, the device 52 may have a sensor 58 for sensing the energy emitted by the x-ray machine, and triggering the inclinometer 22 to activate at the time of exposure and store the data in memory module 54. The sensor may be sensitive to x-rays directly, or be coupled to the cassette array for indication of an exposure event.

Sensor 58 may also be coupled to an indicator 60, such as an LED or similar lamp, which signals exposure of the cassette array to x-ray radiation. Thus, an illuminated indicator 60 would signal the radiologist or technician that the cassette is already exposed and not to be used for subsequent imaging unless refreshed. The exposure indicator 60 alone provides significant improvement over existing cassettes, as double exposure, or fear of such exposure, is a known and often reported issue for technologists. The exposure indicator 60 may be configured so that the indicator resets upon refreshing the cassette imaging plate.

The device 52 may also (in lieu of or in combination with sensor 58) include manual activation switch 62, such as a depressible button, to initiate retrieval of inclination data. The switch 62 may also be coupled to indicator 60 to warn whether a cassette 50 has been exposed.

In an alternative embodiment, a portion of the reporting device 52, e.g., the digital inclinometer and sensor, may be a portable device that is configured to plug into the cassette 50 via a port (e.g., USB or serial connection). Thus the digital inclinometer may be placed on the cassette at the time of imaging, and be used on subsequent imaging cassettes. The cassette 50 would have a memory module 54 for storing the data obtained from the digital inclinometer, and communication port 56 (i.e., RF transmitter, or the USB connector) for uploading the data and radiographic image to the digitizer at a later time.

Figure 11:
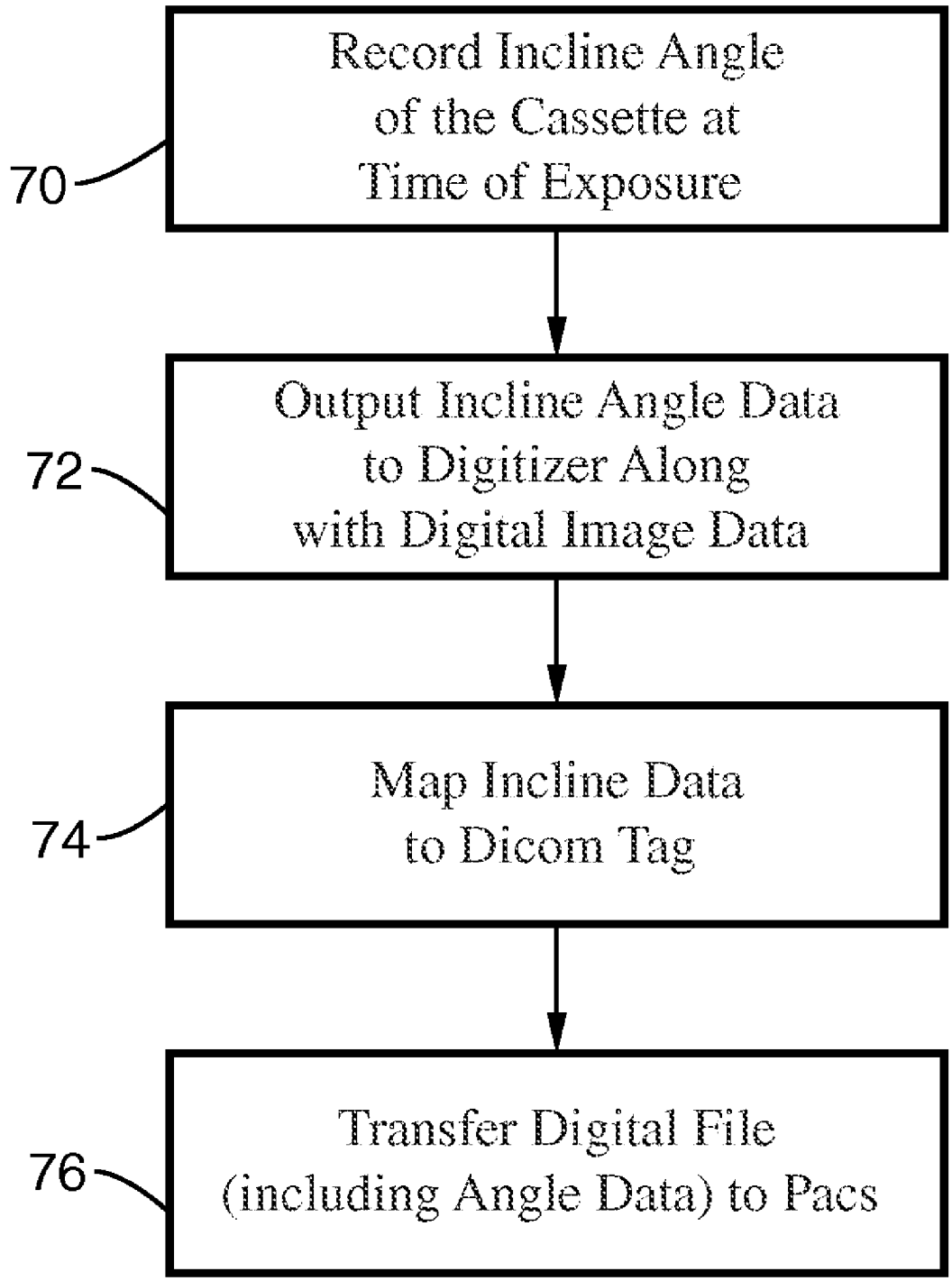
FIG. 11 is a flow diagram of a method of recording angle of inclination of a radiographic digital cassette in accordance with the present invention.

FIG. 11 illustrates a method of recording angle of inclination of a radiographic digital cassette in accordance with the present invention. After the clinician orders an imaging study, a technologist usually receives the requisition, and transports the x-ray device and imaging cassettes to the patient. At the time of x-ray exposure (or just before), the incline angle of the cassette is recorded relative to gravity at step 70. This can be achieved either through manual activation by technologist, or automatic detection via a sensor or the like. At step 72, the cassette is placed in digitizer for processing, and angle of incline data (along with other data stored on the cassette) is passed to the digitizer (either via radiofrequency, direct pin connection, or the like). The angle of incline data may be transferred before, during, or after radiographic image processing that is normally performed by the digitizer. At step 74, the angle data mapped to DICOM tag, and incorporated into the digital file. The digital file transferred to PACS for interpretation at step 76, where the inclination angle data is stored in DICOM file with image data to be viewed at any later date or time.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. An apparatus for measuring an angle of inclination of a radiographic imaging cassette, comprising:
    a digital inclinometer configured to measure an angle of inclination of the cassette with respect to gravity;
    a display coupled to the inclinometer for indicating the angle of inclination of the cassette; and
    a power source for delivering power to the digital inclinometer;
    wherein the display comprises radio-opaque gradations such that the angle of inclination is recorded on an image processed from the imaging cassette.

2. An apparatus as recited in claim 1, wherein the digital inclinometer comprises a micro-electromechanical system (MEMS) accelerometer.

3. An apparatus as recited in claim 1, wherein the display comprises a digital readout.

4. An apparatus as recited in claim 1, wherein the display is configured to indicate angular inclination based on an analog voltage output from the digital inclinometer.

5. An apparatus as recited in claim 4, wherein the angle of inclination is scaled linearly with the analog output voltage.

6. An apparatus as recited in claim 1, further comprising:
    means for detachably mounting the digital inclinometer to the imaging cassette.

7. A radiographic imaging cassette, comprising:
    a cassette comprising an imaging plate responsive to radiographic photons and a casing supporting the imaging plate;
    a digital inclinometer coupled to the casing and configured to measure an angle of inclination of a surface of the cassette with respect to gravity;
    a memory module coupled to the digital inclinometer;
    a power source for delivering power to the digital inclinometer and memory module; and
    an output device for communicating the angle of inclination.

8. A radiographic imaging cassette as recited in claim 7, wherein the output device comprises a wireless transmitter.

9. A radiographic imaging cassette as recited in claim 8, wherein the output device comprises a radio frequency (RF) transmitter.

10. A radiographic imaging cassette as recited in claim 7, wherein the output device is also configured to transmit patient related data.

11. A radiographic imaging cassette as recited in claim 7, further comprising:
    a sensor coupled to the digital inclinometer, the sensor detecting exposure to radiographic photons.

12. A radiographic imaging cassette as recited in claim 11, wherein the sensor is configured to initiate a reading from the digital inclinometer.

13. A radiographic imaging cassette as recited in claim 12, wherein the sensor is coupled to an indicator for signaling exposure of the cassette to radiographic photons.

14. A radiographic imaging cassette as recited in claim 7, further comprising:
    a manual switch to initiate a reading from the digital inclinometer.

15. A method for reporting an angle of inclination of a radiographic imaging cassette, comprising:
    measuring an angle of inclination of an imaging cassette with respect to gravity via an accelerometer;

generating an electric signal from the accelerometer corresponding to the angle of inclination with respect to gravity; and displaying the angle of inclination of the imaging cassette.

16. A method as recited in claim 15, wherein generating an electric signal comprises:

generating a digital signal corresponding to the angle of inclination of the cassette; and wherein displaying the angle of inclination comprises displaying the angle of inclination on a digital readout.

17. A method as recited in claim 15, wherein generating an electric signal comprises:

generating an analog signal corresponding to the angle of inclination of the cassette; and wherein displaying the angle of inclination comprises displaying the angle of inclination on an analog display.

18. A method as recited in claim 17, wherein the analog display comprises radio-opaque gradations, the method further comprising:

recording the angle of inclination on an image processed from the imaging cassette.

19. A method as recited in claim 17, wherein displaying the angle of inclination of the imaging cassette comprises scaling the angle of inclination linearly with an analog output voltage generated from the accelerometer.

20. A method for reporting an angle of inclination of a radiographic imaging cassette, comprising:

generating angle of inclination data of an imaging cassette with respect to gravity via an accelerometer;

generating a digital signal from the accelerometer corresponding to the angle of inclination data; and uploading the angle of inclination data to a digitizer for processing.

21. A method as recited in claim 20, further comprising:

storing the angle of inclination data in a memory module prior to uploading the data to a digitizer.

22. A method as recited in claim 20, wherein uploading the angle of inclination data comprises wirelessly uploading to a digitizer.

23. A method as recited in claim 22, wherein uploading the angle of inclination data comprises wirelessly uploading to a digitizer via a radio frequency (RF) signal.

24. A method as recited in claim 20, further comprising:

mapping the angle of inclination data to a DICOM (Digital Imaging and Communications in Medicine) tag.

25. A method as recited in claim 24, further comprising:

generating a digital file comprising angle of inclination data and the angle of inclination data DICOM tag.

26. A method as recited in claim 25, further comprising:

viewing the angle of inclination data simultaneously with the radiographic image.

27. A method as recited in claim 20, further comprising:

initiating generation of the angle of inclination data prior to or during exposure of the cassette to a radiographic image.

28. A method as recited in claim 27, wherein initiating generation of the angle of inclination data comprises detecting the exposure of the cassette to radiographic x-rays.

29. A method as recited in claim 28, further comprising:

visually indicating the detection of exposure of the cassette to the radiographic x-rays.

30. A method as recited in claim 27, wherein initiating generation of the angle of inclination data comprises manually initiating a reading from the digital inclinometer.

\* \* \* \* \*